United States Patent
Bertrand et al.

(10) Patent No.: US 8,765,992 B2
(45) Date of Patent: Jul. 1, 2014

(54) PREPARATION OF CHALCONE DERIVATIVES

(75) Inventors: Karine Bertrand, Frelinghein (FR); Alice Roudot, Lomme (FR); Patrice Rool, Brunoy (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 13/698,832

(22) PCT Filed: May 16, 2011

(86) PCT No.: PCT/EP2011/057903
§ 371 (c)(1),
(2), (4) Date: Feb. 4, 2013

(87) PCT Pub. No.: WO2011/144579
PCT Pub. Date: Nov. 24, 2011

(65) Prior Publication Data
US 2013/0131372 A1    May 23, 2013

(30) Foreign Application Priority Data

May 17, 2010 (EP) .................... 10305519

(51) Int. Cl.
*C07C 321/00* (2006.01)
*C07C 323/00* (2006.01)
*C07C 381/00* (2006.01)

(52) U.S. Cl.
USPC ............................................. 560/9

(58) Field of Classification Search
CPC .... C07C 319/20; C07C 67/31; C07C 319/12; C07C 323/22; C07C 45/45; C07C 67/08; C07C 69/738
USPC ................................. 560/53, 9; 568/315, 43
See application file for complete search history.

(56) References Cited

U.S. PATENT DOCUMENTS

| 5,089,654 | A * | 2/1992 | Yokomori et al. ............... 560/53 |
| 2005/0176808 | A1 | 8/2005 | Najib et al. |
| 2006/0142611 | A1 | 6/2006 | Delhomel et al. |
| 2007/0032543 | A1 | 2/2007 | Delhomel et al. |
| 2011/0190515 | A1 | 8/2011 | Najib |

OTHER PUBLICATIONS

Written Opinion of the International Searching Authority for PCT/EP2011/057903, mailed Sep. 26, 2011.

* cited by examiner

*Primary Examiner* — Brandon Fetterolf
*Assistant Examiner* — Blaine G Doletski
(74) *Attorney, Agent, or Firm* — Nixon & Vanderhye P.C.

(57) ABSTRACT

The invention relates to methods for producing chalcone (1,3-diphenylprop-2-en-1-one) derivatives that have multiple substitutions on a phenyl ring. Intermediate chalcone derivatives are modified by Phase Transfer Catalysis (PTC) for introducing a substituted alkyl group that is provided by a sulfonic acid derivative on a phenyl ring already containing substituent groups on one or two carbon atoms adjacent to the carbon atom where a substituent group is being introduced. The methods of the invention allow producing efficiently, by either S-alkylation or O-alkylation, chalcones derivatives that are characterized for their biological activities that are intermediate compounds for producing molecules having such activities, or that can be used for generating libraries of compounds to be screened by means of in vitro and/or in vivo assays and establishing structure-activity relationships.

17 Claims, No Drawings

PREPARATION OF CHALCONE DERIVATIVES

This application is the U.S. national phase of International Application No. PCT/EP2011/057903, filed 16 May 2011, which designated the U.S. and claims priority to EP Application No. 10305519.0, filed 17 May 2010, the entire contents of each of which are hereby incorporated by reference.

TECHNICAL FIELD

The invention relates to methods for producing chalcone derivatives substituted on at least one of the two phenyl groups by multiple substituent groups.

BACKGROUND

Chalcones (1,3-diaryl-2-propen-1-ones) are open chain flavonoids that have an enone moiety between two aromatic rings. As recently reviewed (Batovska D and Todorova I, 2010; Patil C et al., 2009; Go M et al., 2005), different families of natural chalcones have been isolated from plant extracts and characterized as having relevant biological properties such as antioxidant, cytotoxic, anticancer, antibiotic, antiinfective, hypoglycaemic, and anti-inflammatory activities.

Chalcone derivatives are used, or are under development, for medical uses, as well as like food additives and cosmetic formulation ingredients, and the pharmacological potential of chalcone derivatives is considered to be not yet fully exploited. In that respect, libraries of synthetic chalcone derivatives have been generated and screened using animal models, cell-based assays and/or biochemical assays, in order to establish structure-activity relationships and identify compounds having improved biological properties (such as target specificity, potency, bioavailability, and/or safety) or chemical features (such as stability or lipophilicity). Thus, chalcone is considered as a template molecule that can be adapted to desired activities by introducing specific chemical moieties and/or conformational restraints (Katsori A and Hadjipavlou-Litina D, 2009; Jamal H et al., 2008; Chimenti F et al., 2009; Sivakumar P et al., 2009; Henmi K et al., 2009; Srinivasan B et al., 2009; Patil C et al., 2009; Rao G et al., 2009; Reddy M et al., 2008; Alberton E et al., 2008; Romagnoli R et al., 2008; Gacche R et al., 2008; Liu X et al., 2008a; Hachet-Haas M et al., 2008; Chiaradia L et al., 2008; Cabrera M et al., 2007; Jung S et al., 2006; Go M et al., 2005; Ansari F et al., 2005; US20070092551).

In particular, there are several examples of natural or synthetic chalcone derivatives that contain at least an aromatic ring with substitutions on adjacent carbon atoms. For example, Licochalones, Derricin, and other natural chalcone variants show antibacterial or antiparasitic activity, cytotoxic activity against human cancerous cells, or proapoptotic activity on endothelial cells (Cunha G at al., 2003; Yoon G et al., 2005; Ghayur M et al., 2006; Ogawa Y et al., 2007; Matsuura M et al., 2001; Na Y et al., 2009; Tsukiyama R et al., 2002; Zhu X et al., 2005). Libraries of synthetic Licochalcone variants or conjugates have been produced and tested in various models (Kromann H et al., 2004; Yoon G et al., 2009; Liu X et al., 2008b).

The biological activities of natural or synthetic chalcone derivatives that have multiple substitutions on one or both phenyl groups have been described, such as insulin-mimetic action (US20070092551), anti-inflammatory activities (WO 01/98291), or inhibition of angiogenesis (WO 01/046110). Chalcone derivatives containing substituent groups on at least three adjacent (or consecutive) carbon atoms of a phenyl ring (such as those described in WO 04/005233, WO 05/073184, WO 07/147,879, WO 07/147,880, and U.S. Pat. No. 7,524, 975) are activators of one or more Peroxisome Proliferator-Activated Receptors (PPARs), a family of nuclear receptors that are therapeutic targets, in particular for treating metabolic or neurodegenerative disorders (Akiyama T et al., 2005; Gross B and Staels B, 2007).

Generally, synthetic chalcone derivatives are produced by a Claisen-Schmidt condensation reaction of an aldehyde with a ketone, but other approaches are possible, such as palladium-catalysed reactions (Patil C. et al., 2009; Katsori A. and Hadjipavlou-Litina D., 2009). However, the acidic nature of the obtained compound and the frequent presence in the reaction medium of secondary products and unreacted starting materials require additional steps of purification and/or specific approaches, such as microwave irradiation, that result in a significant reduction in the yield and/or make difficult the later modifications of these compounds. In fact, chalcone derivatives can be used as starting materials for producing other classes of compounds such as flavonoids or pyrazoles.

Phase transfer catalysis, which is considered as a reliable strategy for the asymmetric synthesis of organic compounds in simple experimental conditions, mild reaction conditions, and for large-scale preparations, has been used to the modify chalcone derivatives through condensation of intermediate compounds, as well as epoxidation or Michael addition of chalcone derivatives (Ooi T and Marouka K, 2007; Song G and Ahn B, 1994; Li J and Liu X, 2008; Rao G et al., 2009).

The synthesis and/or further modification of chalcone derivatives that contain at least a phenyl ring with substituent groups on adjacent carbon atoms of the ring can be inefficient due to steric hindrance. Alternative synthetic strategies for producing such chalcone derivatives, in particular by either S-alkylation or O-alkylation, have been described in the literature cited above and elsewhere (WO 05/005369, WO 04/056727). However, the need for novel methods allowing the efficient production of chalcone derivatives that have multiple substitutions, and in particular on adjacent carbon atoms of a phenyl ring, is still clear and urgent.

SUMMARY OF INVENTION

The present invention provides highly efficient methods for producing chalcone derivatives with multiple substitutions on a phenyl ring. Intermediate chalcone derivatives are modified by Phase Transfer Catalysis (PTC) for introducing a substituted alkyl group that is provided by a sulfonic acid derivative on a phenyl ring already containing substituent groups on one or two carbon atoms adjacent to the carbon atom where the substituent group is being introduced.

The methods of the invention allow producing efficiently, by either S-alkylation or O-alkylation, chalcones derivatives that are characterized for their biological activities that are intermediate compounds for producing molecules having such activities, and/or that can be used for generating libraries of compounds to be screened by means of in vitro and/or in vivo assays and establishing structure-activity relationships.

Further objects of the present invention are provided in the Detailed Description.

DETAILED DESCRIPTION OF THE INVENTION

The present invention provides methods for producing compounds that contain two phenyl groups linked to each other, wherein one of said phenyl groups is substituted in at least two (and preferably at least three) positions, a conformation that characterize compounds having medical interest but that can make the later modification of one of such positions poorly efficient due to the steric hindrance. This effect occurs when the size of groups within a molecule prevents chemical reactions in a specific position, limiting the possibilities of generating variants of natural or synthetic compounds having biological and pharmaceutical activities, such as chalcone derivatives for which the literature shows the importance of having multiple substituents on a single phenyl ring.

The invention provides methods for producing chalcone derivatives of General Formula ($I_b$) by using appropriate reactants and conditions for applying Phase Transfer Catalysis (PTC), in particular by either S-alkylation or O-alkylation. These reactants and conditions are not disclosed in the prior art as being applicable for the synthesis of chalcone derivatives of General Formula ($I_b$). Moreover, as shown in the Examples, a series of 1,3-diphenylprop-2-en-1-ones has been successfully produced according to the Invention with improved yields and purity.

In the main embodiment, the present invention provides a method for preparing a compound of following General Formula ($I_b$):

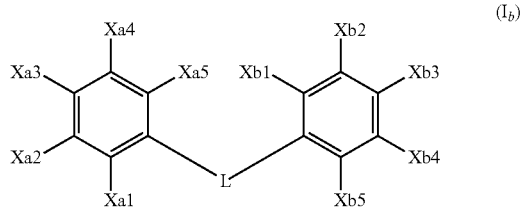

($I_b$)

wherein:

$X_{a1}$, $X_{a2}$, $X_{a3}$, $X_{a4}$, and $X_{a5}$, identical or different, are a hydrogen atom, a halogen atom, a —$R_a$ or -$G_a$-$R_a$ group;

$R_a$ is an alkyl, an alkenyl, a cycloalkyl, an aryl, an alkyloxy, an alkylthio, or a heterocyclic group, said group can be substituted or not, or $R_a$ is a protecting group linked to the phenyl ring by an oxygen atom or sulfur atom;

L is a CO—$R_L$ or $R_L$—CO group;

$X_{b1}$, $X_{b2}$, $X_{b3}$, $X_{b4}$, and $X_{b5}$ are substituent groups, wherein one of them is a $R'_b$-$G_b$-$R_c$ or $G_b$-$R_c$ group, and at least one of other substituent groups adjacent to said $R'_b$-$G_b$-$R_c$ or $G_b$-$R_c$ group is a halogen atom or a $R''_b$ group, the remaining groups being independently hydrogen atoms, halogen atoms or $R''_b$ groups;

$R''_b$ is an alkyl, an alkenyl, a cycloalkyl, an aryl, an alkyloxy, an alkylthio, or a heterocyclic group, said group can be substituted or not, or $R''_b$ is a protecting group linked to the phenyl ring by an oxygen atom or sulfur atom;

$R'_b$ is an alkyl, an alkenyl, a cycloalkyl, an aryl, an alkyloxy, an alkylthio, or a heterocyclic group, said group can be substituted or not;

$R_L$ is an unsubstituted or substituted alkyl or alkenyl group;

$G_a$ and $G_b$, identical or different, are an oxygen atom or sulfur atom;

$R_c$ is an alkyl group substituted by at least a —$COOR_d$ group, wherein $R_d$ is an unsubstituted alkyl, alkenyl, aryl, cycloalkyl, or heterocyclic group;

Said method comprising the following steps:
a) Obtaining the compound of General Formula ($I_a$):

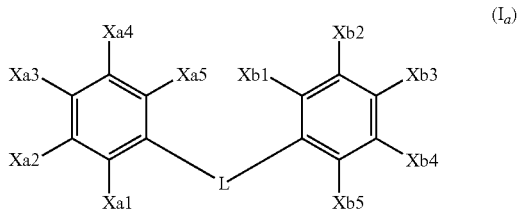

($I_a$)

in which $X_{a1}$, $X_{a2}$, $X_{a3}$, $X_{a4}$, $X_{a5}$, L, $R_a$, $R'_b$, $R''_b$, $R_L$, $G_a$, and $G_b$ group are defined as for General Formula ($I_b$); and $X_{b1}$, $X_{b2}$, $X_{b3}$, $X_{b4}$, and $X_{b5}$ are substituent groups wherein one of them is a $R'_b$-$G_b$-H or $G_b$-H group, and at least one of the substituent groups adjacent to said $R'_b$-$G_b$-H or $G_b$-H group is a halogen or a $R''_b$ group, the remaining groups being independently hydrogen atoms, halogen atoms or $R''_b$ groups;

b) contacting the compound of General Formula ($I_a$) with a sulfonic acid derivative of General Formula (II): $R_s$—$SO_2$—O—$R_c$, in a biphasic organic solvent/water medium, and in presence of a compound of General Formula (III):

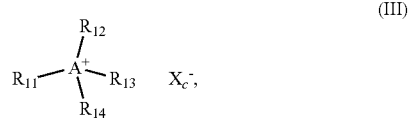

(III)

in which:

$R_s$, $R_{t1}$, $R_{t2}$, $R_{t3}$, and $R_{t4}$, identical or different, are unsubstituted alkyl groups;

A is a nitrogen or phosphorus atom;

$X_c$ is an halogen, $HSO_4$, or $H_2PO_4$ and $R_c$ is as defined for General Formula ($I_b$).

In the context of the invention, whenever $X_{a1}$, $X_{a2}$, $X_{a3}$, $X_{a4}$, or $X_{a5}$ is a —$R_a$ or $G_a$-$R_a$ group, $G_a$ stands for $G_{a1}$, $G_{a2}$, $G_{a3}$, $G_{a4}$, or $G_{a5}$ respectively and $R_a$ stands for $R_{a1}$, $R_{a2}$, $R_{a3}$, $R_{a4}$, or $R_{a5}$, respectively. The same applies to $X_{b1}$, $X_{b2}$, $X_{b3}$, $X_{b4}$, and $X_{b5}$: whenever $X_{b1}$, $X_{b2}$, $X_{b3}$, $X_{b4}$, or $X_{b5}$ is a —$R_b$ or -$G_b$-$R_b$ group, $G_b$ stands for $G_{b1}$, $G_{b2}$, $G_{b3}$, $G_{b4}$, or $G_{b5}$ respectively and $R_b$ stands for $R_{b1}$, $R_{b2}$, $R_{b3}$, $R_{b4}$, or $R_{b5}$, respectively.

In the context of the present invention, the term "alkyl" refers to a saturated hydrocarbon radical that is linear or branched, having preferably from one to seven carbon atoms (such as methyl, ethyl, n-propyl, isopropyl, n-butyl, isobutyl, tert-butyl, sec-butyl, pentyl, neopentyl, or n-hexyl), and more preferably from one to four carbon atoms.

The term "alkenyl" refers to a non-saturated hydrocarbon (with at least one double carbon bond) radical that is linear, branched or cyclic, having preferably from two to seven carbon atoms, (such as ethenyl, 1-propenyl, 2-propenyl, 1-butenyl, 2-butenyl, 1-pentenyl, 2-pentenyl, 3-methyl-3-butenyl radical) and more preferably from two to four carbon atoms.

The terms "alkyloxy" and "alkylthio" refer to alkyl groups as defined above that are linked to the remainder of the compound by an oxygen or a sulfur atom (thioether bond) respectively.

The term "cycloalkyl" designates an alkyl group as defined above that forms one or more cycle(s) having preferably from three to fourteen carbon atoms, such as cyclopropyl, cyclobutyl, cyclopentyl, cyclohexyl, cycloheptyl, and cyclooctyl.

The term "aryl" designates an aromatic group, having preferably from six to twelve carbon atoms such as phenyl, naphthyl, biphenyl, or anthracenyl.

The term "heterocyclic" refers to a heterocycloalkyl group or a heteroaryl group, that is a cycloalkyl or an aryl group, as indicated above, that further comprises one or more heteroatoms selected among nitrogen, oxygen or sulfur. They generally comprise from four to fourteen carbon atoms, such as morpholinyl, piperidinyl, or tetrahydropyranyl.

The term "halogen" refers to a bromine, chlorine, fluorine or iodine atom.

The alkyl, alkenyl, alkyloxy, alkylthio, cycloalkyl, aryl, or heterocyclic groups can be substituted. These substituent groups are preferably halogen atoms, alkyl, alkenyl, aryl groups as defined above, or any functional group protected by a protecting group, such as defined below. Whenever $R_a$, $R''_b$ or $R'_b$ is a substituted alkyl, alkenyl, cycloalkyl, aryl, alkyloxy, alkylthio, or heterocyclic group, said group is preferably substituted by at least one halogen atom.

The term "protecting group" means a chemical moiety that is permanently or preferably temporarily reacted with a functional group of a compound used to obtain a compound of General Formula ($I_a$) so as to protect said functional group from a subsequent reaction, the protecting group can thereafter be selectively removed in a further step from the corresponding compound without altering its structure. Said protecting group is consequently not reactive under the conditions of the methods of the Invention and it allows obtaining a selective modification of a different moiety of the corresponding compound of General Formula ($I_a$). Literature discloses many appropriate protecting groups ("Green's Protective Groups in Organic Synthesis" 2007, ed. Wuts P and Greene T, John Wiley & Sons Inc.).

A $R_a$ group and/or a $R''_b$ group can be a protecting group that is linked to the phenyl ring by an oxygen atom or sulfur atom, in case where the compounds used to obtain compounds of General Formula ($I_a$) present at least one OH or SH group, in addition to the one ($R'_b$-$G_b$-H or a $G_b$-H group) that is to be alkylated according to the method of the Invention. This protecting group is intended to avoid undesirable reactions of the additional OH or SH group during the PTC reaction.

The compounds of General Formula ($I_a$) that present the $R'_b$-$G_b$-H or a $G_b$-H group and are used according to the Invention are generally obtained by using the reaction schemes known from the literature which involve either the purification from plant extracts (as for natural chalcone derivatives), or a condensation, such a Claisen-Schmidt reaction between an acetophenone and a benzaldehyde (see Example 1 and Scheme 1). The condensation reaction can be carried out in acidic or basic medium, according to the specific reactants, and with or without microwave irradiation. Preferably, the two starting materials are contacted in stoichiometric proportions and the reaction is carried out at room temperature (between approximately 18° C. and 25° C.) and at atmospheric pressure. In basic medium, the reaction is preferably carried out in the presence of a strong base, such as an alkaline metal hydroxide, like NaOH, or an alkaline metal alcoholate such as sodium ethylate. In acidic medium, the reaction is preferably carried out in the presence of a strong acid, such as hydrochloric acid.

Other methods for the synthesis of chalcone derivatives that can be used according to the methods of the Invention are described in the literature (Patil C et al., 2009, Katsori A and Hadjipavlou-Litina D, 2009). For instance, palladium-based catalysis can be used for performing the Suzuki coupling between an activated benzoic acid with multiple substitutions and a phenyl vinylboronic acid, or for the coupling of a halophenol with an (un)substituted 1-aryl-2-propen-1-ol that leads to the synthesis of dihydrochalcones.

The compounds of General Formula ($I_a$) or ($I_b$) may also be provided in a form containing an isotope (radioactive or not) of hydrogen, carbon, sulphur, or oxygen atoms that help detecting the compounds after their administration or during their purification. The compound of General Formula ($I_a$) or ($I_b$) may also contain one or several asymmetrical centres. An enantiomerically pure (or enriched) preparation of a compound of General Formula ($I_a$) or ($I_b$) can be obtained either by stereospecific purification of the final product, or by asymmetrical synthesis, as described in the literature ("Chirality in Drug Design and Development" 2004, ed. Reddy I and Mihvar R, CRC Press).

Compounds of General Formula ($I_a$) can contain protecting groups in one or more positions. Such protecting groups may be needed depending on the type of further chemical modification that is desirable for specific compounds of General Formula ($I_b$) since they can allow a precise modification either by PTC itself, or by other chemical reactions to which the compound of the General Formula ($I_b$) resulting from the PTC reaction is submitted to. Some examples include alcohol or phenol protecting groups (wherein the protecting group is linked to the phenyl group by means of an oxygen atom) or thiol or thiophenol protecting groups (wherein the protecting group is linked to the phenyl group by means of a sulfur atom). For instance, if an additional —OH group should be present in a position of one phenyl ring (such as in many natural chalcone derivatives), the compound of General Formula ($I_a$) or ($I_b$) can present a phenol protecting group as $R_a$ or $R''_b$ substituent group in that specific position.

The methods of the Invention, with or without further chemical transformations of the resulting compounds, allow establishing structure-activity relationships that apply not only to known compounds of General Formula ($I_b$) and their biological properties (as generally established for chalcone derivatives, or even improved) but also to additional structural variants for which structural and/or biological properties may not have been identified, and which can be used and/or tested according to the desired biological activity.

Specific additional chemical reactions can be implemented for the preparation of drug candidate molecules, in particular by applying technologies that allow simplifying synthetic protocols, such as polymer-assisted solution-phase synthesis or microwave-assisted organic synthesis, and establishing a workflow for medicinal chemists (Carey J et al., 2006; Colombo M and Peretto 1,2008; Jordan A and Roughley S, 2009). Moreover, cheminformatics and computer-aided drug design techniques may allow a more systematic qualitative and quantitative evaluation of chemical libraries to identify structure-property relationships and potential drug candidates that deserve being synthesized and tested for their biological activities (Di L et al., 2009; Song C et al., 2009; Zhao H and Guo Z, 2009; Villar H and Hansen M, 2009; Wishart D, 2008; Mayr L and Bojanic D, 2009).

The literature provides examples of compounds of General Formula ($I_a$) and ($I_b$) that have been produced and characterized as having biological activities of interest (WO 04/005233; WO 05/073184; see Table 3). The literature also provides examples of compounds of General Formula ($I_a$) that have been either isolated from plant extracts or synthesized, and characterized as having biological properties of interest (Zhu X et al., 2005; Ghayur M et al., 2006; Batovska D and Todorova 1,2010; Cunha G at al., 2003; Na Y et al., 2009; Ogawa Y et al., 2007; Matsuura M et al., 2001; US20070092551). The structure of compounds of General Formula $(I_b)$ can be further modified using reaction schemes that are known in the literature for drug candidates and/or for chalcone derivatives in general, and that are compatible with the physico-chemical features of such compounds. Such modifications of the structures can be envisioned as to identify novel compounds of medical interest. Examples of such modifications are epoxydation, reduction, hydrolysis, or reactions that allow producing other classes of compounds such as flavonoids or pyrazoles (Patil C et al., 2009; Ooi T and Maruoka K, 2007; Carey J et al., 2006; WO 07/147,879; WO 04/005233; U.S. Pat. No. 7,208,447).

The compounds of General Formula $(I_a)$ and/or $(I_b)$ can be purified by precipitation or solid/liquid extraction after evaporation of the reaction medium. Further or other purification step can be performed by chromatography over silica gel or by crystallization, when the compound is stable as a solid form, by applying techniques well known in the literature for chalcone derivatives or, more in general, for chemicals ("Purification of Laboratory Chemicals", 2009, ed. Armarego W and Chai C; Elsevier). Moreover, the required purification and/or (re-)crystallization steps that are appropriate for isolating compounds of General Formula $(I_a)$ and/or $(I_b)$ from the reaction mixture can be used for obtaining amorphous, polymorphous, mono- or poly-crystalline forms. Such polymorphs may present distinct pharmacological and/or chemical properties, for example in terms of solubility, intrinsic dissolution rate, melting temperature, bioavailability, and/or possible transition from a polymorphic state to another one in pharmaceutical compositions and/or biological fluids.

The (re-)crystallisation assays can be performed in panels of different solvents (such as isopropanol, acetone, methanol, diisopropyl ether, or water) or mixture thereof, and by applying different conditions, such as reaction volumes or temperatures. The resulting samples can be analyzed by different techniques such as microscopy, calorimetry, and/or spectroscopy that allow establishing the features of a particular crystalline form, such as structure, solubility, stability or conversion to other forms (Erdemir D et al., 2007; Bauer M, 2004; Morissette S et al., 2004; Yin S and Grosso J, 2008). Such a polymorphism study allows characterizing the crystalline form of a compound that is pharmaceutically acceptable for both pharmacological and manufacturing points of view.

In particular, compounds of General Formula $(I_b)$ can be obtained as specific salts, hydrates, and polymorphs that can be obtained during the final purification step of the compound or, in the case of salts, by incorporating the salt into the previously purified compound. The selection of a compound of General Formula $(I_b)$ that is produced according to the methods of the Invention as an optimal candidate for drug development can be automated for a comprehensive biopharmaceutical characterization at the scale-up stage and for the solid or liquid formulation that is appropriate for the desired route of administration and therapeutic indication (Kumar L et al., 2007; <<Handbook of Pharmaceutical Salts Properties, Selection, and Use>> 2002; edit. Stahl P and Wermuth G; Viley-VCH Germany; <<Pharmaceutical Dosage Forms and Drug Delivery>> 2007, ed. Mahato R, CRC Press).

The methods of the Invention can be applied to known compounds of General Formula $(I_a)$ that present specific types of substituent groups and combinations thereof, as well as to novel variants of these known compounds that comprise one or more substituent groups compatible with the Methods of the Invention, in particular regarding the need of a single, specific position presenting a $R'_b$-$G_b$-H or a $G_b$-H, to be modified by O-alkylation or S-alkylation, and the absence of other substituent groups that may decrease the efficiency of the PTC reaction.

In a preferred embodiment of the Invention, $R_L$ group is an unsubstituted alkyl or an alkenyl group having from two to seven carbon atoms, and more preferably two carbon atoms, so that L is CO—CH=CH, CO—$CH_2$—$CH_2$, CH=CH—CO or $CH_2$—$CH_2$—CO. Alternatively, if the $R_L$ group is a substituted alkyl or alkenyl group, the substitution is preferably an alkyl group that is linked to the carbon atom linked to the —CO group in L, so that the chalcone derivative is the s-trans conformation (Go M et al., 2005).

When $R_L$ group of General Formula $(I_a)$ and $(I_b)$ is a $CH_2$—$CH_2$ group, these compounds are dihydrochalcone (1,3-diphenylpropan-1-one) derivatives. Such compounds can also be prepared following the reduction of the corresponding 1,3-diphenylprop-2-en-1-one of General Formula $(I_b)$ in which L represents a CO—CH=CH (see scheme 1), as described for example in WO 07/147,879.

Then, depending on the choice of the orientation in which L is positioned between the two phenyl rings (and the type and/or number of substituent groups that provide biological activities on such phenyl rings), the compounds of General Formula $(I_a)$ and $(I_b)$ can represent synthetic or natural chalcone derivatives having various medical uses (Batovska D. and Todorova I., 2010; Katsori A and Hadjipavlou-Litina D, 2009; Go M et al., 2005). Preferably, the L of General Formula $(I_a)$ and $(I_b)$ is a CO—$R_L$ group.

In another particular embodiment of the Invention, only one of the substituent groups among $X_{a1}$, $X_{a2}$, $X_{a3}$, $X_{a4}$, and $X_{a5}$ of General Formula $(I_a)$ and $(I_b)$ is a halogen, a $R_a$ or $G_a$-$R_a$ group and the other four substituent groups among $X_{a1}$, $X_{a2}$, $X_{a3}$, $X_{a4}$, and $X_{a5}$ groups are hydrogen atoms. Alternatively, two or three of the substituent groups of General Formula $(I_a)$ and $(I_b)$ among $X_{a1}$, $X_{a2}$, $X_{a3}$, $X_{a4}$, and $X_{a5}$ groups, identical or different, are a halogen, a $R_a$ or $G_a$-$R_a$ group as defined above (and therefore different from hydrogen atoms). The positions that can be more preferably substituted with a halogen, a $R_a$ or $G_a$-$R_a$ group are chosen among $X_{a1}$, $X_{a3}$, and $X_{a5}$, $X_{a3}$ being the most preferably substituted position as shown in Example 1 wherein $X_{a3}$ is a halogen, an alkyloxy or an alkylthio group. Alternatively, $R_a$ is preferably an unsubstituted alkyl group having from one to seven carbon atoms.

In another particular embodiment of the Invention, the $X_b$ substituent group of General Formula $(I_a)$ that, following step (b) of the methods of the Invention becomes a $G_b$-$R_c$ group is preferably a $G_b$-H group. In particular, $G_b$ is preferably an oxygen atom (in order to pursue an O-alkylation) and more preferably there is no $R_a$ or $G_a$-$R_a$ group present in the other phenyl ring. Alternatively, $G_b$ is preferably an oxygen atom and the compounds of General Formula $(I_a)$ and $(I_b)$ present a single $R_a$ or $G_a$-$R_a$ group. In this latter case, $G_a$ is preferably a sulphur atom.

Moreover, the $X_b$ substituent group of General Formula $(I_a)$ that is an $R'_b$-$G_b$-H or a $G_b$-H group is $X_{b1}$ or $X_{b3}$ and even more preferably it is $X_{b3}$. Thus, among the $X_{b1}$, $X_{b2}$, $X_{b3}$, $X_{b4}$, and $X_{b5}$ of General Formula $(I_a)$ and $(I_b)$ that are not the $R'_b$-$G_b$-H or $G_b$-H group, at least two of them, identical or different, are preferably a halogen or a $R''_b$ group, one being an $X_b$ adjacent to the $X_b$ that is a $R'_b$-$G_b$-H or $G_b$-H group, and the remaining substituent group(s) being hydrogen atom(s). In particular:

if $X_b$, of General Formula $(I_a)$ is the $R'_b$-$G_b$-H or $G_b$-H group, $X_{b2}$ is the adjacent group that is a halogen or a $R''_b$ group, wherein at least either $X_{b4}$ or $X_{b5}$ are preferably halogen or a $R''_b$ group;

if $X_{b2}$ of General Formula ($I_a$) is the $R'_b$-$G_b$-H or $G_b$-H group, $X_b$, and/or $X_{b3}$, identical or different, are adjacent groups that are halogen(s) or $R''_b$ group(s), wherein at least $X_b$, and $X_{b3}$, $X_{b3}$ and $X_{b5}$, or $X_b$, and $X_{b5}$ are preferably halogen or a $R''_b$ group;

if $X_{b3}$ is the $R'_b$-$G_b$-H or the $G_b$-H group, $X_{b2}$ and/or $X_{b4}$, identical or different, are the adjacent groups that are halogen(s) or $R''_b$ group(s), wherein at least $X_{b2}$ and $X_{b4}$, $X_{b2}$ and $X_{b5}$ or $X_b$, and $X_{b2}$ are preferably halogen or a $R''_b$ group.

In any of the combinations listed above, the $X_b$ groups that are neither the $R'_b$-$G_b$-H or $G_b$-H group nor a hydrogen atom, are preferably identical or different $R''_b$ groups being unsubstituted alkyl groups or alkyloxy groups, more preferably having from one to seven carbon atoms, and even more preferably from one to four carbon atoms.

The compounds of General Formula ($I_b$) preferably comprise $R_c$ and $R_d$ that are identical or different alkyl groups having from one to seven carbon atoms, and even more preferably unsubstituted alkyl groups having from one to four carbon atoms.

The structural and functional analysis of known compounds of following General Formula ($I_a$) and ($I_b$) shows that specific substituent groups are present in compounds known to have biological activities. Example 2 and Table 3 provide details on the specific compounds that can be used and/or produced according to the Invention, wherein:

$X_{a1}$ $X_{a2}$, $X_{a4}$, and $X_{a5}$ are a hydrogen atom;

$X_{a3}$ is a hydrogen atom, a halogen, a $R_a$ or $G_a$-$R_a$ group;

L is a CO—CH=CH, CO—CH$_2$—CH$_2$, CH=CH—CO, or CH$_2$—CH$_2$—CO group;

$X_{b1}$, $X_{b2}$, $X_{b3}$, $X_{b4}$, and $X_{b5}$, identical or different, are substituent groups wherein:

i) if $X_{b1}$ is the $R'_b$-$G_b$-H or a $G_b$-H group of Formula ($I_a$) that becomes a $R'_b$-$G_b$-$R_c$ or a $G_b$-$R_c$ group of Formula ($I_b$), $X_{b2}$ is a halogen or an unsubstituted alkyl or aryl group;

$X_{b3}$ is a an alkyloxy, or a alcohol or a phenol protecting group linked to the phenyl ring by an oxygen atom or sulfur atom;

$X_{b4}$ is a hydrogen or an unsubstituted alkyl or aryl group;

$X_{b5}$ is a hydrogen or an alkyloxy group;

ii) if $X_{b3}$ is the $R'_b$-$G_b$-H or a $G_b$-H group of Formula ($I_a$) that becomes a $R'_b$-$G_b$-$R_c$ or a $G_b$-$R_c$ group of Formula ($I_b$), either at least one between $X_{b2}$ and $X_{b4}$ is a halogen or an unsubstituted alkyl or aryl group and at least one between $X_{b1}$ and $X_{b5}$ is an alkyloxy, or an alcohol or a phenol protecting group linked to the phenyl ring by an oxygen atom or sulfur atom; or $X_{b2}$ and $X_{b4}$ are unsubstituted alkyl groups and $X_{b1}$ and $X_{b5}$ are hydrogen atoms.

In case (i), compounds such as Derricin (Cunha G et al., 2003) or 98c (Batovska D and Todorova I, 2010) can be used in step (a) of the methods of the invention for generating variants that can be tested for improved, or additional, biological features when compared to the original compounds.

In case (ii), either specific Licochalcones (Na Y et al., 2009) or specific 1,3-diphenylprop-2-en-1-ones derivatives (WO 04/005233; WO 05/073184) can be used according to the Invention as compounds of General Formula ($I_a$).

The synthesis of the following compounds is described, according to the Methods of the Invention, in the Examples:

Cpd. 1a: 1-[4-methylthiophenyl]-3-[3,5-dimethyl-4-hydroxyphenyl]prop-2-en-1-one (intermediate compound 2 of WO2004/005233);

Cpd. 1b: 1-[4-methylthiophenyl]-3-[3,5-dimethyl-4-tertbutyloxycarbonyl-dimethyl methyloxyphenyl]prop-2-en-1-one (compound 27 of WO2004/005233);

Cpd. 2a: 1-[4-methylthiophenyl]-3-[3,5-diethyl-4-hydroxyphenyl]prop-2-en-1-one;

Cpd. 2b: 1-[4-methylthiophenyl]-3-[3,5-diethyl-4-tertbutyloxycarbonyl-dimethylmethyloxyphenyl]prop-2-en-1-one;

Cpd. 3a: 1-[4-methylthiophenyl]-3-[3,5-diisopropyl-4-hydroxyphenyl]prop-2-en-1-one;

Cpd. 3b: 1-[4-methylthiophenyl]-3-[3,5-diisopropyl-4-tertbutyloxycarbonyl-dimethylmethyloxyphenyl]prop-2-en-1-one;

Cpd. 4a: 1-[4-methylthiophenyl]-3-[3,5-dimethyl-4-hydroxyphenyl]prop-2-en-1-one (intermediate compound 2 of WO2004/005233);

Cpd. 4b: 1-[4-methylthiophenyl]-3-[3,5-dimethyl-4-ethyloxycarbonyl-dimethylmethyloxy phenyl]prop-2-en-1-one Cpd. 5a: 1-[4-trifluoromethyloxyphenyl]-3-[3,5-dimethyl-4-hydroxyphenyl]prop-2-en-1-one Cpd. 5b: 1-[4-trifluoromethyloxy]-3-[3,5-dimethyl-4-ethyloxycarbonyl-dimethylmethyloxy phenyl]prop-2-en-1-one Cpd. 6a: 1-[4-chlorophenyl]-3-[3,5-dimethyl-4-hydroxyphenyl]prop-2-en-1-one (intermediate compound 2 of WO2004/005233);

Cpd. 6b: 1-[4-chlorophenyl]-3-[3,5-dimethyl-4-tertbutyloxycarbonyl-dimethylmethyloxy phenyl]prop-2-en-1-one (compound 16 of WO2004/005233);

The methods of the Invention require the synthesis and/or purification of the alkylating agent in the form of a sulfonic acid derivative of General Formula (II) that provides the $R_c$ group for the phase transfer reaction according to step (b) defined above, and that is required for the S-alkylation or O-alkylation. In particular, the sulfonic acid derivative of General Formula (II) preferably comprises an $R_s$ which is an alkyl group having from one to four carbon atoms (e.g. methyl methanesulfonate). The sulfonic acid derivative of General Formula (II) is preferably the mesylate of the desired $R_c$ group which is a substituted alkyl groups, as defined above. Such compounds can be either commercially available or synthesized starting from mesyl chloride and the appropriate alcohol of the desired $R_c$ in the presence of a base, in particular an amine base such as triethylamine.

The phase transfer catalyst of General Formula (III) is preferably chosen among commercially available compounds such as methyltrioctylammonium chloride (ALIQUAT® 336), tetrabutylammonium bromide, tetrabutylphosphonium bromide, methyl-(C8-C10)-trialkylammonium chloride (ADOGEN® 464), and tetrabutylammonium hydrogensulfate. Preferably, the compound of General Formula (III) contains a nitrogen atom as A.

The expression "phase transfer catalyst" refers to material that catalyzes a reaction between a moiety that is soluble in a first phase, e.g., an organic phase, and another moiety that is soluble in a second phase, e.g., an aqueous phase. The organic solvent to be included in the biphasic organic solvent/water medium is preferably selected from halogenated solvents, preferably dichloroethane, esters, preferably ethyl acetate, ethers preferably diisopropyl ether, aromatic solvents such as xylene, benzene or toluene, the latter ones being the more preferable. The percentage of the organic solvent in the biphasic organic solvent and water medium is comprised between 10% and 90% in volume, and preferably between 25% and 75%.

The PTC reaction can be performed by applying conditions that provide the better results in terms of yield and/or purity of the compounds of General Formula ($I_b$), as shown in the Examples, or as established when considering known methods for PTC reactions.

Such conditions may be adapted to the amount, ratio, and/or nature of reactants, and comprise the reaction temperature and pressure, the ratios of the compounds, the reflux gas, the addition of a further catalyst, the length of the reaction, or the way (for example the number of times) in which the sulfonic acid derivative of General Formula (II) is added. In particular, the phase transfer catalysis is advantageously carried out at a temperature comprised between 25 and 120° C., and more preferably between 80 and 120° C., preferably at atmospheric pressure. The inert gas is preferably nitrogen and the additional catalyst can be cesium or potassium carbonate. The reaction is carried out with at least one equivalent of compound of General Formula ($I_a$) and of the sulfonic acid derivative of General Formula (II), and pursued for a period of time (for example, at least 12 hours). If appropriate, the sulfonic acid derivative of General Formula (II) and/or the additional catalyst may be further added, and said addition step is optionally repeated (for example 1, 2 or 3 times). Consequently, the reaction may continue until its completion for 24, 48 or more hours, before proceeding to the purification as described above.

DESCRIPTION OF THE TABLES/SCHEMES

Scheme 1—Synthesis of a Family of Compounds of General Formula ($I_a$)

The Examples below provide a detailed description of the synthesis of a specific family of compounds of General Formula ($I_a$) that can be used for generating the corresponding compounds of General Formula ($I_b$), which can be further modified within the linker group between the phenyl rings or in one or more substituent groups of a phenyl ring by reduction, epoxidation or hydrolysis reaction (Panel A). An exemplary reaction scheme for generating such family of compounds of General Formula ($I_a$) is shown (Panel B).

Table 1—Comparison of Methods for the Synthesis of Compounds of General Formula ($I_b$)

A series of specific compounds of General Formula ($I_a$) have been synthesized (Cpd. 1a, 2a, 3a, 4a, 5a, and 6a) and used for generating compounds of General Formula ($I_b$) with appropriate substitutions on the phenyl rings in order to demonstrate the feasibility and the advantages in performing the synthesis of the compounds of General Formula ($I_b$) according to the Invention (Cpd. 1b, 2b, 3b, 4b, 5b, and 6b; Panel A). The comparative analysis of yield and purity has been performed by using different alkylating agents, either already described in the literature for modifying chalcones (AAG 1), or examples of those to be used according to the methods of the Invention (AAG 2 and AAG 3; Panel B).

Table 2—Alternative Conditions for Applying the Methods of the Invention

Different Phase Transfer conditions (c1-c7) have been tested to compare the yield and purity with which a specific compound of General Formula ($I_b$) is obtained with AAG 2.

Table 3—Examples of compounds of General Formula ($I_a$) and ($I_b$)

This non-exhaustive summary provides several examples of compounds of General Formula ($I_a$) that can be used for generating compounds of General Formula ($I_b$) having different structural and biological properties according to the methods of the Invention. Compounds of General Formula ($I_b$) can potentially be further modified on the substituent groups and/or the linker, in particular by epoxidation, hydrolysis, reduction, or deprotection (see also the Detailed Description and Example 2).

Scheme 1

A)

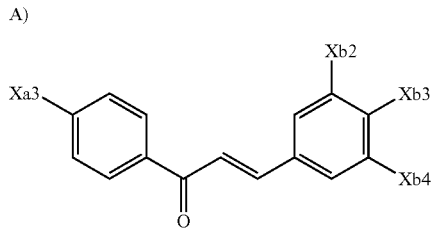

Compounds of General Formula ($I_a$) wherein:
L is a CO—CH═CH group;
$X_{a1}$, $X_{a2}$, $X_{a4}$, $X_{a5}$, $X_{b1}$, and $X_{b5}$ are H;
$X_{a3}$ is a halogen, a $R_a$, or $G_a$-$R_a$ group;
$X_{b2}$ and $X_{b4}$, identical or different, are a halogen or a $R''_b$ group:
$X_{b3}$ ia a $G_b$-H group Phase Transfer Catalyzed O or S alkylation:
$R_s$—$SO_2$—O—$R_c$ (sulfonic acid derivative of General Formula (II), wherein $R_s$ is an unsubstituted alkyl group and $R_c$ is an alkyl group substituted by a —$COOR_d$ group, wherein $R_d$ is an alkyl group;
nBu$_4$NHSO$_4$ (quaternary ammonium salt of General Formula (III))

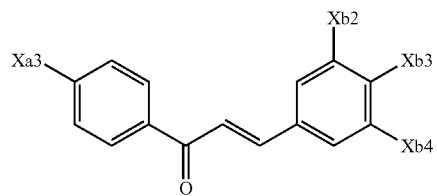
Compounds of General Formula (Ib) wherein:
L is a CO—CH=CH group;
$X_{a1}$, $X_{a2}$, $X_{a4}$, $X_{a5}$, $X_{b1}$, and $X_{b5}$ are H;
$X_{a3}$ is a halogen, a $R_a$, or $G_a$-$R_a$ group;
$X_{b2}$ and $X_{b4}$, identical or different, are a halogen or a $R''_b$ group:
$X_{b3}$ is a $G_b$-$R_c$ group
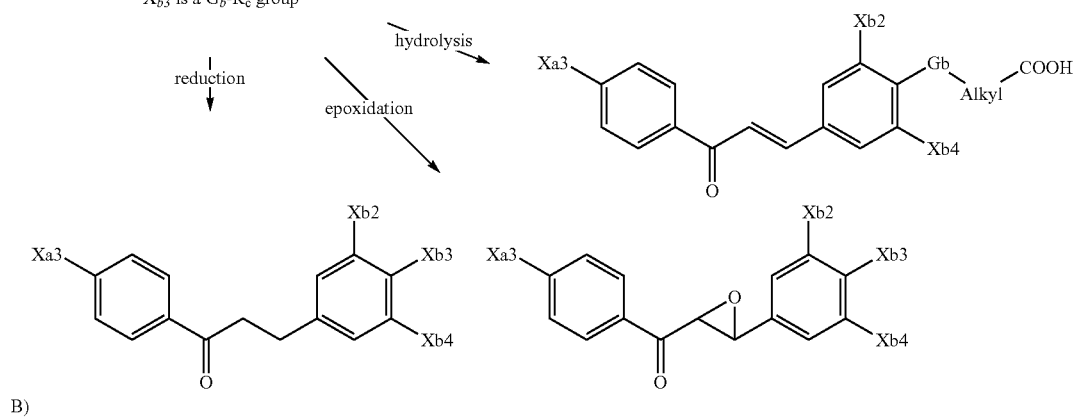
B)
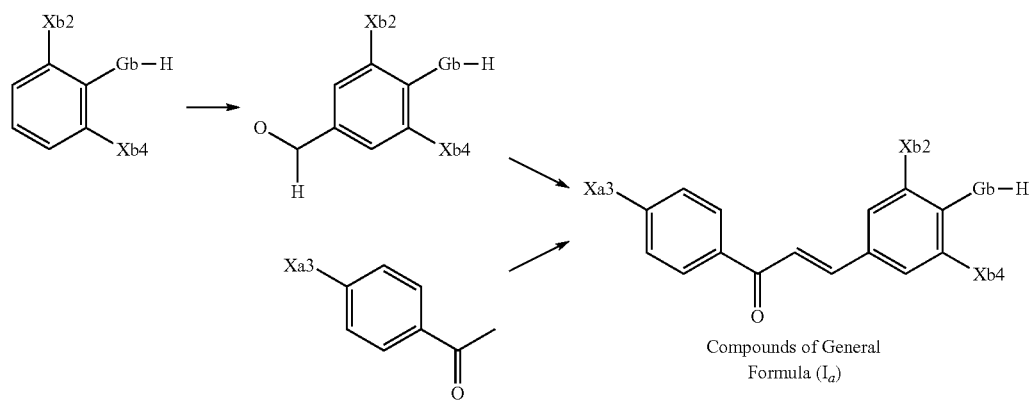
TABLE 1
A)
Compounds of General Formula ($I_a$)
Cpd. 1a
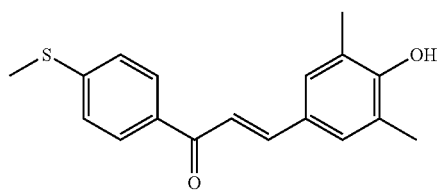

TABLE 1-continued
Cpd. 2a
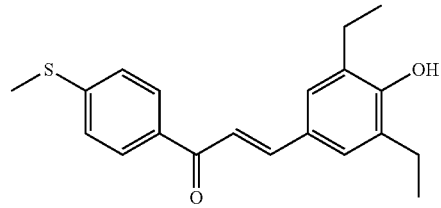 [SMILES: CCc1cc(/C=C/C(=O)c2ccc(SC)cc2)cc(CC)c1O]
Cpd. 3a
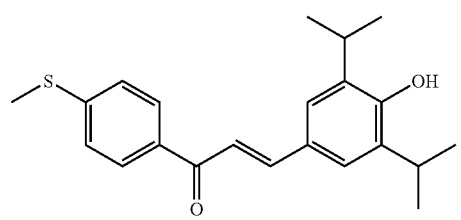 [SMILES: CSc1ccc(C(=O)/C=C/c2cc(C(C)C)c(O)c(C(C)C)c2)cc1]
Cpd. 4a
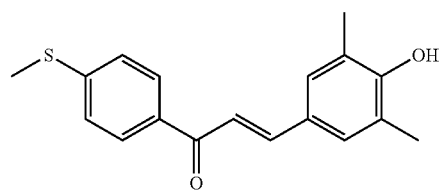
Cpd. 5a
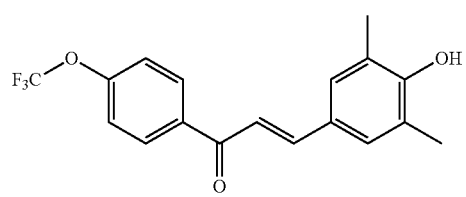 [SMILES: Cc1cc(/C=C/C(=O)c2ccc(OC(F)(F)F)cc2)cc(C)c1O]
Cpd. 6a
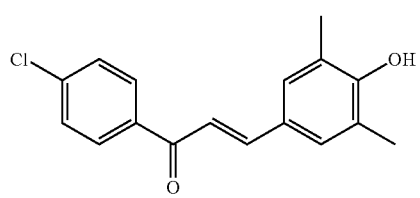 [SMILES: Cc1cc(/C=C/C(=O)c2ccc(Cl)cc2)cc(C)c1O]
Compounds of General Formula ($I_b$)
Cpd. 1b
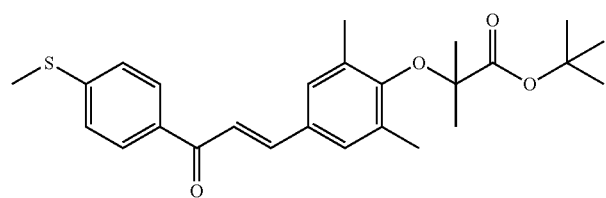 [SMILES: CSc1ccc(C(=O)/C=C/c2cc(C)c(OC(C)(C)C(=O)OC(C)(C)C)c(C)c2)cc1]
Cpd. 2b
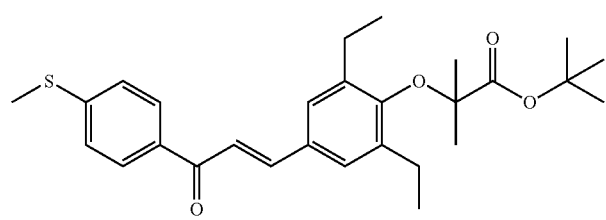 [SMILES: CCc1cc(/C=C/C(=O)c2ccc(SC)cc2)cc(CC)c1OC(C)(C)C(=O)OC(C)(C)C]

TABLE 1-continued
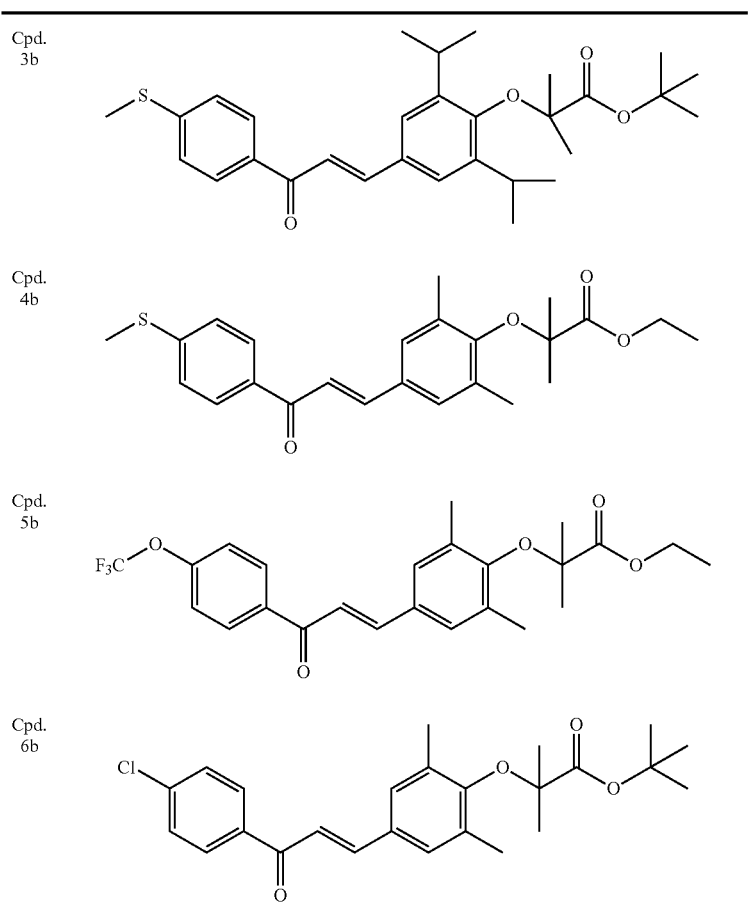
| B) | | | | | | |
|---|---|---|---|---|---|---|
| Compound of General Formula (I$_a$) | | | | Compound of General Formula (I$_b$) | | |
| Cpd. | Xb2, Xb4 | Xa3 | AAG* | Cpd. | Yield (%) | Purity (%) |
| 1a | CH$_3$— | CH$_3$—S— | AAG1 | 1b | 6 | 4 |
|  |  |  | AAG2 |  | 75 | 98 |
| 2a | CH$_3$CH$_2$— |  | AAG1 | 2b | 16 | 16 |
|  |  |  | AAG2 |  | 65 | 93 |
| 3a | (CH$_3$)$_2$CH— |  | AAG1 | 3b | 12 | 35 |
|  |  |  | AAG2 |  | 44 | 64 |
| 4a | CH$_3$— | CH$_3$—S— | AAG3 | 4b | 72 | Not Determined |
| 5a |  | CF$_3$—O— |  | 5b | 33 |  |
| 6a |  | Cl | AAG2 | 6b | 58 |  |
*AAG1 is: 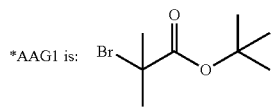
AAG2 is: 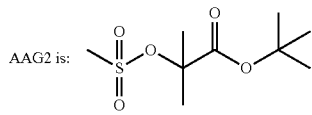
AAG3 is: 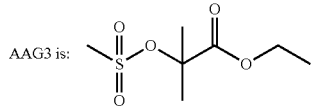

TABLE 2

| No. | Phase Transfer Catalysis Conditions applied to Cpd. 1a | | Resulting Cpd. 1b | |
|---|---|---|---|---|
| | Solvent (% in the mixture) | Catalyst (% in the mixture) | Yield (%) | Purity (%) |
| c1 | Toluene (50%) | $nBu_4NHSO_4$(5%) | 57 | 92 |
| c2 | | $nBu_4NHSO_4$(10%) | 75 | 98 |
| c3 | | $nBu_4NHSO_4$(20%) | 70 | 98 |
| c4 | | $nBu_4PBr$(10%) | 76 | 99 |
| c5 | | $CH_3N[(CH_2)_7-CH_3]_3Cl$ (10%) | 75 | 94 |
| c6 | Toluene (25%) | $nBu_4NHSO_4$ (10%) | 50 | 92 |
| c7 | Toluene (75%) | | 77 | 96 |

TABLE 3

| Families of known compounds of General Formula (Ia) | Examples of such compounds of General Formula (Ia) | Corresponding compounds of General formula (Ib) that can be produced |
|---|---|---|
| Intermediate compounds having General Formula (Ia) wherein: L is a CO—CH═CH group; Only one Xa group is a halogen, a Ra, or a Ga—Ra group (the other Xa groups being H) Xb1 and Xb5 are H; Xb2 and Xb4 are a halogen or a R″b; Xb3 is a Gb—H group | Intermediate compounds 1, 2, 4, 8, and 9 of WO 04/005233 (wherein Xa3 is the substituted group) Intermediate compound 3 of WO 04/005233 (wherein Xa1 or Xa5 is the substituted group) Intermediate compounds 1-4, 8, 13, and 18 of WO 05/073184 (wherein Xa3 is the substituted group) | Compounds 15, 16, 27, 28, 32, 38 and 40 of WO 04/005233 (PPAR activators; then, compounds 17, 29, 33, 39 and 41 of WO 04/005233 can be produced by acid hydrolysis) Compound 30 of WO 04/005233 (PPAR activator; then, compound 31 of WO 04/005233 can be produced by acid hydrolysis) Compounds 1, 5, 7 10, 22, 32, and 44 of WO 05/073184 (PPAR activators; then, compounds 2, 6, 8, 11, 23, 33 and 45 of WO 05/073184 can be produced by acid hydrolysis) |
| Intermediate compounds having General Formula (Ia) wherein: L is a CO—CH═CH group; at least two Xa groups are a halogen, a Ra, or a Ga—Ra group (the other Xa groups being H) Xb1 and Xb5 are H; Xb2 and Xb4 are a halogen or a R″b; Xb3 is a Gb—H group | Intermediate compounds 7 of WO 04/005233, and 14, 15, 17, and 19 of WO 05/073184 (wherein Xa3 or Xa2 and Xa5 or Xa4 are substituted groups) Intermediate compounds 5-7, 9, 10, 12, and 16 of WO 05/073184 (wherein at least Xa2 and Xa3 are substituted groups) | Compounds 36 of WO 04/005233 and 34, 36, 40, and 46 of WO 05/073184 (PPAR activators; then, compounds 37 of WO 04/005233 and 35, 37, 41, and 47 of WO 05/073184 can be produced by acid hydrolysis) Compounds 12, 16, 20, 24, 26, 30, and 38 of WO 05/073184 (PPAR activators; then, compounds 13, 17, 21 25, 27, 31, and 39 of WO 05/073184 can be produced by acid hydrolysis) |
| Natural/synthetic chalcone derivatives having various biological activities and presenting: at least 3 substitutions on only one phenyl ring, at least two of these substitutions are on adjacent carbon atoms, one of them being an —OH group (═Gb—H ), with or without a single substitution on the other phenyl ring (═Ra) | ON-III (Zhu X et al., 2005) SS-2, SS-3 (Ghayur M et al., 2006) Cpd 34a, 34b, 98c (Batovska D and Todorova I, 2010) Derricin (Cunha G at al., 2003) Licochalcones A, C, D, E (Na Y et al., 2009) Cpd. 36, 38, C035 (US20070092551) Cpd 5c, 98d (Batovska D and Todorova I, 2010) Cpd 4 (Ogawa Y et al., 2007) 4-hydroxyderricin (Matsuura M et al., 2001) | Synthetic variants of these compounds wherein the hydroxy group becomes an O—Rc group, to be tested for their biological activities (if an additional —OH are present in the original compound, as in the licochalcones or 4-hydroxyderricin, this group can be previously modified with a protective group to be later eliminated or substituted) |

All references cited herein are fully incorporated by reference in their entirety. Having now fully described the Invention, it will be understood by those of skill in the art that the Invention may be practiced within a wide and equivalent range of conditions and parameters, without affecting the scope of the Invention or any embodiment thereof.

EXAMPLES

Example 1

Comparative Synthesis of Compounds of General Formula ($I_b$)

Materials & Methods
Synthesis of the Compounds of General Formula ($I_a$) in Acidic Medium Cpd. 1a and Cpd. 4a have been synthesized. 4'-methylthioacetophenone (1 equivalent) and 3,5-dimethyl-4-hydroxybenzaldehyde (1 equivalent) were dissolved in ethanol solution saturated with gaseous hydrochloric acid. Reaction was stirred at room temperature for 6 hours and solvent was eliminated by vacuum evaporation. Compounds were purified by chromatography on silica gel (elution in cyclohexane/ethyl acetate).

Cpd. 2a and Cpd. 3a have been synthesized and purified similarly to Cpd. 1a, using 4'-methylthioacetophenone and either 3,5-diethyl-4-hydroxybenzaldehyde or 3,5-diisopropyl-4-hydroxybenzaldehyde, respectively, as starting materials.

Cpd. 5a and Cpd. 6a have been synthesized and purified similarly to Cpd. 1a, using 3,5-dimethyl-4-hydroxybenzaldehyde and either 4'-trifluoromethoxyacetophenone or 4'-chloroacetophenone, respectively as starting materials.
Synthesis of the Compounds of General Formula (Ib) by Phase Transfer Catalysis (PTC)

The PTC reactions were performed using AAG1 (tert-butyl α-bromoisobutyrate, Sigma-Aldrich ref. 17455), AAG2 (tert-butyl 2-methyl-2-(methylsulfonyloxy)propanoate), or AAG3 (ethyl 2-methyl-2-(methylsulfonyloxy)propanoate) as alkylating agent.

Each PTC reaction was performed under nitrogen atmosphere using 10 g of a compound of General Formula ($I_a$), 1.5 equiv. of potassium carbonate, in presence of tetra-n-butylammonium hydrogen sulfate ($nBu_4NHSO_4$; compound of General Formula (III), at the amount corresponding to 10% of compound of General Formula ($I_a$)). The reactants were mixed in 100 mL of solvent (50% water/50% toluene) and the mixture was heated up to 80° C. before adding 1.0 equivalent of AAG1, AAG2, or AAG3. The mixture was then kept under reflux for 22 hours, 1.0 equivalent of potassium carbonate and a 2nd aliquot of 1.0 equivalent of AAG1, AAG2, or AAG3 were added. After that the mixture was kept under reflux for further 22 hours, 1.0 equivalent of potassium carbonate and a 3rd 1.0 equivalent of AAG1, AAG2, or AAG3 were added. The mixture was kept under reflux for further 22 hours, the mixture was then returned to room temperature and 50 mL of ethyl acetate were added. After decantation and washing twice with water (50 mL) and brine (50 mL), the organic layer was evaporated to dryness. The solid residue was purified by chromatography over silica gel (for Cpd. 2b, 3b, and 4b) or crystallized in 20 mL of diisopropyl ether (for Cpd. 1b, 5b, and 6b). In the latter case after reflux for 1 hour, the mixture was cooled to 0° C. with ice bath and kept at this temperature for 1 hour. Solid material was collected, washed with cold diisopropyl ether and dried under vacuum.

Results & Conclusions

The methods of the invention are intended to improve the efficiency with which compounds of General Formula ($I_a$) can be modified by either O- or S-alkylation and compounds of General Formula ($I_b$) are produced in conditions of steric hindrance. At this scope a series of reactions were set up for generating exemplary compounds of General Formula ($I_a$) to be used for comparing the efficiency of the coupling reaction by PTC (Table 1). At this scope, different alkylating agents were evaluated in Phase Transfer reactions applied to with different compounds of General Formula ($I_a$), but maintaining constant other parameters of the reaction (amount of reactants, solvent, length of the reaction, etc.), allowing a better comparison of the methods.

The results clearly shows that the percentage of the yield and of the purity of the desired compound of General Formula ($I_b$), as assessed by HPLC analysis, is well superior (at least two fold, as in the case of Cpd. 3b) whenever AAG2 or AAG3 (compounds according to General Formula (II), and not a brominated derivative as in AAG1) are used for inserting the desired group in a position of a phenyl ring comprised between two positions already modified with an alkyl groups (Table 1). Thus the superiority of the methods of the Invention, when it is compared to the known methods (such as those described in WO 04/005233 or WO 05/005369) was clearly demonstrated for a panel of representative compounds of General Formula ($I_a$), ($I_b$), and (II).

Example 2

Additional Requirements for Applying the Methods of the Invention

Materials & Methods
Reactants and Conditions for Phase Transfer Catalysis

The synthesis of Cpd. 1a and the purification of Cpd. 1b were performed as described in Example 1. The PTC condition that were maintained constant were: the amount of Cpd. 1a (10 g), the specific alkylating agent and the number of equivalents (AAG2, 3.0 equivalents that are added in three time=3 equivalents), the number of day of reflux (3 days), the volume of solvent (10 volumes, compared to Cpd. 1a), the purification (by the crystallisation of crude Cpd. 1b in 2 volumes of diisopropyl ether).
Results & Conclusions:

Additional conditions of the coupling reaction by phase transfer catalysis according to the invention were tested in order to generate data which can be compared to each other regarding alternative ways to perform the methods of the Invention, and in particular the proportion of the organic solvent in the mixture with water and the amount and/or the nature of the phase transfer catalyst (Table 2). It has been demonstrated that alternative conditions according to the methods of the Invention can provide satisfactory, if not improved, yield and/or purity of a compound of General Formula ($I_b$).

The methods of the Invention can be adapted to the synthesis of compounds of pharmaceutical interest that are disclosed in the literature (Table 3). In a first series of examples, chalcone derivatives of General Formula ($I_b$) that have been characterized as PPAR activators can be generated by means of the methods of the Invention starting from appropriate intermediate compounds of General Formula ($I_a$) present in WO 04/005233 and WO 05/073184. Alternatively, natural or synthetic chalcone derivatives of General Formula ($I_a$) having various biological activities present multiple substitutions on either one and/or the other phenyl ring, including one or more —OH groups. These compounds can be used as starting point for generating novel variants of known compounds that comprise a $R_c$ group in a predefined position where O-alkylation is performed according to the Invention (for instance, by adding a protecting group in the —OH groups not to be modified by PTC), and that can be tested and validated for any relevant biological activities.

REFERENCES

Akiyama T et al., 2005. Curr Diab Rep. 5: 45-52.
Alberton E et al., 2008. Chem Biol Interact. 171: 355-62.
Ansari F et al., 2005. Chem Biodivers. 2: 1656-64.
Batovska D and Todorova I, 2010. Curr Clin Pharmacol. 5: 1-29.
Bauer M, 2004. STP Pharma Pratiques. 14: 281-291.
Carey J et al., 2006. Org Biomol Chem. 4: 2337-47.
Cabrera M et al., 2007. Bioorg Med. Chem. 15: 3356-67.
Chiaradia L et al., 2008. Bioorg Med Chem. 16: 658-67.
Chimenti F et al., 2009. J Med Chem. 52: 2818-24.
Colombo M and Peretto I, 2008. Drug Discov Today. 13: 677-84.
Cunha G at al., 2003. Phytother Res. 17: 155-9.
Di L et al., 2009. Curr Pharm Des. 15: 2184-94.
Erdemir D et al., 2007. Curr Opin Drug Discov Devel. 10: 746-55.
Gacche R et al., 2008. Chem Pharm Bull. 56: 897-901.
Ghayur M et al., 2006. Phytother Res. 20: 49-52.
Go M et al., 2005. Curr Med Chem. 12: 481-99.
Gross B and Staels B, 2007. Best Pract Res Clin Endocrinol Metab. 21: 687-710.
Hachet-Haas M et al., 2008. J Biol Chem. 283: 23189-99.
Henmi K et al., 2009. Biol Pharm Bull. 32: 1109-13.
Jamal H et al., 2008. Fundam Clin Pharmacol. 22: 673-81.
Jordan A and Roughley S, 2009. Drug Discov Today. 14: 731-44.
Jung S et al., 2006. Chem Pharm Bull. 54: 368-71.
Kamal A et al., 2008. Bioorg Med Chem Lett. 18: 2434-9.
Katsori A and Hadjipavlou-Litina D, 2009. Curr Med Chem. 16: 1062-81.
Kromann H et al., 2004. Eur J Med Chem. 39. 993-1000.
Kumar L et al., 2007. Drug Discov Today. 12: 1046-53.
Li J and Liu X, 2008. Ultrason Sonochem. 15: 330-3.
Liu X et al., 2008. Bioorg Med Chem. 16: 171-80.
Liu X et al., 2008b. Eur J Med Chem. 43: 1681-7.
Matsuura M et al., 2001. Planta Med. 67: 230-5.
Mayr L and Bojanic D, 2009. Curr Opin Pharmacol. 9: 580-8.
Morissette S et al., 2004. Adv Drug Deliv Rev. 56: 275-300.
Na Y et al., 2009. Chem Pharm Bull. 57: 607-9.
Ogawa Y et al., 2007. Chem. Pharm. Bull. 55: 675-8.
Ooi T and Marouka K, 2007. Angew. Chem. Int. Ed. 46: 4222-4266;
Patil C et al., 2009. J. Pharm. Sci. & Res. 1: 11-22.
Rao G et al., 2009. Eur J Med Chem. 44: 2239-45.
Reddy M et al., 2008. Bioorg Med Chem. 16: 7358-70.
Romagnoli R et al., 2008. Bioorg Med Chem. 16: 5367-76.
Sivakumar P et al., 2009. Chem Biol Drug Des. 74: 68-79.
Song C et al., 2009. Brief Bioinform. 10: 579-91.
Song G and Ahn B, 1994. Arch Pharm Res. 17: 434-7.
Srinivasan B et al., 2009. J Med Chem. 52: 7228-35.
Tsukiyama R et al., 2002. Antimicrob Agents Chemother. 46: 1226-30.
Villar H and Hansen M, 2009. Curr Opin Drug Discov Devel. 12: 367-75.
Wishart D, 2008. Drugs R&D. 9: 307-22
Yoon G et al., 2005. Chem Pharm Bull. 53: 694-5.
Yoon G et al., 2009. Bioorg Med Chem Lett. 19: 5155-7.
Yin S and Grosso J, 2008. Curr Opin Drug Discov Devel. 11: 771-7.
Zhao H and Guo Z, 2009. Drug Discov Today. 14: 516-22.
Zhu X et al., 2005. Mol Pharmacol. 67: 1444-50.

The invention claimed is:
1. A method for preparing a compound of following General Formula ($I_b$):

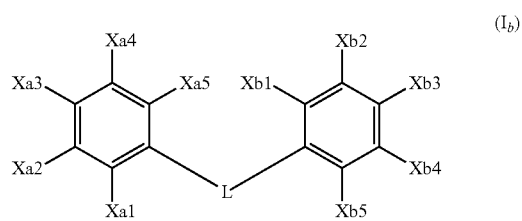

wherein:
$X_{a1}$, $X_{a2}$, $X_{a3}$, $X_{a4}$, and $X_{a5}$, identical or different, are a hydrogen atom, a halogen atom, a $R_a$ or $G_a$-$R_a$ group;
$R_a$ is an alkyl, an alkenyl, a cycloalkyl, an aryl, an alkyloxy, an alkylthio, or a heterocyclic group, said group can be substituted or not, or $R_a$ is a protecting group linked to the phenyl ring by an oxygen atom or sulfur atom;
L is a CO—$R_L$ or $R_L$—CO group;
$X_{b1}$, $X_{b2}$, $X_{b3}$, $X_{b4}$, and $X_{b5}$ are substituent groups, wherein one of them is a $R'_b$-$G_b$-$R_c$ or $G_b$-$R_c$ group, and at least one of other substituent groups adjacent to said $R'_b$-$G_b$-$R_c$ or a $G_b$-$R_c$ group is a halogen atom or a $R''_b$ group, the remaining groups being independently hydrogen atoms, halogen atoms or $R''_b$ groups;
$R''_b$ is an alkyl, an alkenyl, a cycloalkyl, an aryl, an alkyloxy, an alkylthio, or a heterocyclic group, said group can be substituted or not, or $R''_b$ is a protecting group linked to the phenyl ring by an oxygen atom or sulfur atom;
$R'_b$ is an alkyl, an alkenyl, a cycloalkyl, an aryl, an alkyloxy, an alkylthio, or a heterocyclic group, said group can be substituted or not;
$R_L$ is an unsubstituted or substituted alkyl or alkenyl group;
$G_a$ and $G_b$, identical or different, are an oxygen atom or sulfur atom;
$R_c$ is an alkyl group substituted by at least a —COOR$_d$ group, wherein $R_d$ is an unsubstituted alkyl, alkenyl, aryl, cycloalkyl, or heterocyclic group;
said method comprising the following steps:
a) obtaining the compound of General Formula ($I_a$):

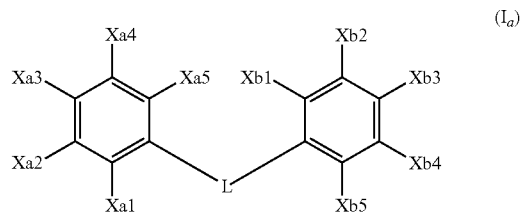

wherein:
$X_{a1}$, $X_{a2}$, $X_{a3}$, $X_{a4}$, $X_{a5}$, L, $R_a$, $R'_b$, $R''_b$, $R_L$, $G_a$, and $G_b$ group are defined above; and $X_{b1}$, $X_{b2}$, $X_{b3}$, $X_{b4}$, and $X_{b5}$ are substituent groups wherein one of them is a $R'_b$-$G_b$-H or $G_b$-H group, and at least one of the substituent groups adjacent to said $R'_b$-$G_b$-H or $G_b$-H group is a halogen or a R"$_b$ group, the remaining groups being independently hydrogen atoms, halogen atoms or R"$_b$ groups;

b) contacting the compound of General Formula (I$_a$) with a sulfonic acid derivative of General Formula (II) R$_s$—SO$_2$—O—R$_c$, in a biphasic organic solvent/water medium, and in presence of a compound of General Formula (III):

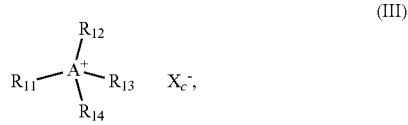

(III)

in which:

R$_s$, R$_{t1}$, R$_{t2}$, R$_{t3}$, and R$_{t4}$, identical or different, are unsubstituted alkyl groups;

A is a nitrogen or phosphorus atom;

X$_c$ is an halogen, HSO$_4$, or H$_2$PO$_4$; and

R$_c$ is defined as for General Formula (I$_b$).

2. The method of claim 1, wherein R$_L$ group is an unsubstituted alkyl or alkenyl group having from two to seven carbon atoms.

3. The method of claim 1, wherein L group is CO—CH=CH, CO—CH$_2$—CH$_2$, CH=CH—CO or CH$_2$—CH$_2$—CO.

4. The method of claim 1, wherein one of the substituent groups among X$_{a1}$, X$_{a2}$, X$_{a3}$, X$_{a4}$, and X$_{a5}$ of General Formula (I$_a$) and (I$_b$) is a halogen, a Ra or Ga—Ra group and the other four substituent groups among X$_{a1}$, X$_{a2}$, X$_{a3}$, X$_{a4}$, and X$_{a5}$ groups are hydrogen atoms.

5. The method of claim 1, wherein X$_{a3}$ of General Formula (I$_a$) and (I$_b$) is a halogen, a R$_a$ or G$_a$-R$_a$ group and the other four substituent groups among X$_{a1}$, X$_{a2}$, X$_{a4}$, and X$_{a5}$ groups are hydrogen atoms.

6. The method of claim 1, wherein the X$_b$ substituent group of General Formula (I$_a$) that, after step (b) becomes a G$_b$-R$_c$ group, is a G$_b$-H group.

7. The method of claim 1, wherein G$_b$ is an oxygen atom.

8. The method of claim 1, wherein the compounds of General Formula (I$_a$) and (I$_b$) present a single R$_a$ or G$_a$-R$_a$ group.

9. The method of claim 1, wherein the X$_b$ substituent group of General Formula (I$_a$) that is a R'$_b$-G$_b$-H or a G$_b$-H group is X$_{b1}$ or X$_{b3}$.

10. The method of claim 1, wherein at least two among the X$_{b1}$, X$_{b2}$, X$_{b3}$, X$_{b4}$, and X$_{b5}$ of General Formula (I$_a$) and (I$_b$) that are not the R'$_b$-G$_b$-H or G$_b$-H group, are a halogen or a R"$_b$ group, one being an X$_b$ adjacent to the X$_b$ that is a R'$_b$-G$_b$-H or G$_b$-H group, and the remaining substituent group(s) being hydrogen atom(s).

11. The method of claim 1, wherein the X$_b$ groups that are neither the R'$_b$-G$_b$-H or G$_b$-H group nor an hydrogen atom, are identical or different R"$_b$ groups being unsubstituted alkyl groups or alkyloxy groups.

12. The method of claim 1, wherein the X$_b$ groups that are neither the R'$_b$-G$_b$-H or G$_b$-H group nor an hydrogen atom, are identical or different R"$_b$ groups being unsubstituted alkyl groups or alkyloxy groups and wherein said X$_b$ groups are X$_{b2}$ and X$_{b4}$.

13. The method of claim 1, wherein the compounds of General Formula (I$_b$) comprise R$_c$ and R$_d$ that are identical or different alkyl groups having from one to seven carbon atoms.

14. The method of claim 1, wherein the sulfonic acid derivative of General Formula (II) is the mesylate of the R$_c$ group.

15. The method of claim 1, wherein the compound of General Formula (III) is of formula (III) wherein A is a nitrogen atom.

16. The method of claim 1, wherein the compound of General Formula (Ib) is further modified using hydrolysis, reduction, or epoxydation reactions.

17. The method according to claim 16, wherein the compound to be modified is of General Formula (Ib), wherein L is a CO—CH=CH group; X$_{a1}$, X$_{a2}$, X$_{a4}$, X$_{a5}$, X$_{b1}$, and X$_{b5}$ are H; X$_{a3}$ is a halogen, a R$_a$, or G$_a$-R$_a$ group; X$_{b2}$ and X$_{b4}$, identical or different, are a halogen or a R"$_b$ group; X$_{b3}$ is a G$_b$-R$_c$ group.

* * * * *